United States Patent

Baijense et al.

(10) Patent No.: US 7,846,977 B2
(45) Date of Patent: Dec. 7, 2010

(54) PROCESSES USING A SUPPORTED CATALYST

(75) Inventors: Cornelis Roeland Baijense, Gameren (NL); Geoffrey Johnson, Aberdeen, NJ (US); Ahmad Moini, Princeton, NJ (US)

(73) Assignee: BASF Corporation, Florham Park, NJ (US)

( * ) Notice: Subject to any disclaimer, the term of this patent is extended or adjusted under 35 U.S.C. 154(b) by 74 days.

(21) Appl. No.: 12/140,740

(22) Filed: Jun. 17, 2008

(65) Prior Publication Data

US 2009/0048353 A1 Feb. 19, 2009

Related U.S. Application Data

(60) Division of application No. 10/836,445, filed on Apr. 30, 2004, and a continuation-in-part of application No. 10/836,445, filed on Apr. 30, 2004, now Pat. No. 7,422,995.

(51) Int. Cl.
*C07C 1/00* (2006.01)
*C07C 211/01* (2006.01)
*B01J 23/00* (2006.01)
*B01J 21/00* (2006.01)
*B01J 20/00* (2006.01)

(52) U.S. Cl. .................. 518/700; 502/253; 502/258; 502/259; 502/260; 502/307; 502/315; 502/316; 502/326; 502/327; 502/329; 502/335; 502/336; 502/337; 502/338; 502/342; 502/343; 502/415; 502/439; 564/463

(58) Field of Classification Search ........... 518/700; 502/253, 258, 259, 260, 307, 315, 316, 326, 502/327, 329, 335, 336, 337, 338, 342, 343, 502/415, 439; 564/463
See application file for complete search history.

(56) References Cited

U.S. PATENT DOCUMENTS

| | | | |
|---|---|---|---|
| 2,488,560 A | | 11/1949 | Reitlinger |
| 4,039,302 A | | 8/1977 | Khera |
| 4,279,830 A | * | 7/1981 | Haag et al. ............ 518/700 |
| 4,826,800 A | | 5/1989 | McAteer |
| 5,006,574 A | | 4/1991 | Sennett et al. |
| 5,208,111 A | | 5/1993 | Decher et al. |
| 5,407,743 A | * | 4/1995 | Clough et al. ............ 428/357 |
| 5,503,840 A | * | 4/1996 | Jacobson et al. ......... 424/421 |
| 5,543,437 A | * | 8/1996 | Benham et al. .......... 518/700 |
| 5,811,365 A | | 9/1998 | Barry |
| 5,945,458 A | | 8/1999 | Barry |
| 6,022,590 A | | 2/2000 | Ferguson |
| 6,103,206 A | * | 8/2000 | Taylor et al. ............. 423/210 |
| 6,551,657 B1 | | 4/2003 | Clough |
| 6,683,024 B1 | | 1/2004 | Khare et al. |
| 6,858,127 B2 | * | 2/2005 | Hoek et al. .............. 208/59 |
| 6,992,041 B1 | | 1/2006 | Yogo et al. |
| 7,052,777 B2 | | 5/2006 | Brotzman et al. |
| 7,084,180 B2 | * | 8/2006 | Wang et al. ............. 518/712 |
| 2004/0260139 A1 | | 12/2004 | Klabunde et al. |

FOREIGN PATENT DOCUMENTS

WO 03/090925 11/2003

OTHER PUBLICATIONS

G. Decher et al., Fuzzy nanoassemblies: toward layered polymeric multicomposites, Science. 1997 p. 1232-1237.
H. Krass et al., Layer-by-layer Self assembly of Polyelectrolyte Bearing Metal Ion Coordination and Electrostatic Functionality, Cham Mater, 2003, pp. 196-203.
G. Decher et al., Buildup of ultrathin multilayer films by a self-assembly process: III. Consecutively alternating adsorption of anionic and cationic poly electrolytes on charged surfaces. Thin Solid Films. 1992 pp. 831-835.
G. Decher et al., Buildup of ultrathin Multilayer Films by a Self-Assembly Process: II. Consecutive Adsorption of Anionic ad Cationic Bipolar Amphiphiles and Polyelectrolytes on Charged Surfaces, Ber Bunsengers Phys. Chem, 1991 pp. 1430-1434.
Yu. Lvov, Assembly, Structural Characterization and Thermal Behavior of Layer-by-Layer Deposited Ultrathin Films of Poly(vinyl sulfate) and Poly(allylamine), Langmuir; The ACS Journal of Surfaces and Colloids, 1993, pp. 481-486.
T. Szabo, et al., Zinc Oxide nanoparticles incorporated in ultrathin layer silicate films and their photocatalytic properties, Colloids and Surfaces A: Physiochem Eng. Aspects, 2004, pp. 23-35.
N. Kovtyukhova et al., Layer-by-Layer self-assembly strategy for template synthesis of nanoscale devices, Materials Science and Engineering C 19, 2003, pp. 255-262.
N. Kovtyukhova, et al., Layer-By-Layer Assembly of Rectifying Junctions in and on Metal Nanowires, J. Phys. Chem. B, 2001, pp. 8762-8769.

* cited by examiner

*Primary Examiner*—Cam N Nguyen
(74) *Attorney, Agent, or Firm*—Raymond F. Keller

(57) ABSTRACT

The present invention relates to a catalyst comprising a preferably oxidic, core material, a shell of zinc oxide around said core material, and a catalytically active material in or on the shell, based on one or more of the metals cobalt, iron, ruthenium and/or nickel, preferably a Fischer-Tropsch catalyst, to the preparation of such a catalyst and the use thereof in GTL processes.

20 Claims, No Drawings

PROCESSES USING A SUPPORTED CATALYST

CROSS-REFERENCE TO RELATED APPLICATION

This application is a divisional of and a continuation-in-part of U.S. patent application Ser. No. 10/836,445, which was filed Apr., 30, 2004 now U.S. Pat. No. 7,422,995 B2 which issued Sep. 9, 2008, which is hereby incorporated by reference.

The invention relates to a heterogeneous catalyst, preferably a Fischer-Tropsch (FT) catalyst suitable for GTL (gas-to-liquid) processes, comprising at least one catalytic metal on a support, to a method for preparing such a catalyst and to processes using such a catalyst.

A catalyst containing cobalt oxide and zinc oxide for use in the synthesis of C1-C3 aliphatic hydrocarbons is known from U.S. Pat. No. 4,039,302.

U.S. Pat. No. 4,826,800 describes a process for preparing a catalyst comprising cobalt and zinc oxide for use after reductive activation as a catalyst in the conversion of synthesis gas to hydrocarbons. The catalyst is prepared by mixing a solution of a soluble zinc salt and a soluble cobalt salt with a precipitant such as ammonium hydroxide or ammonium carbonate and recovering the precipitate.

U.S. Pat. No. 5,945,458 and U.S. Pat. No. 5,811,365 describe a Fischer-Tropsch process in the presence of a catalyst composition of a group VIII metal, e.g. cobalt, on a zinc oxide support. Such a catalyst is made by first preparing the support by adding a solution of zinc salt and other constituents to an alkaline bicarbonate solution. Next, the precipitate is separated from the bicarbonate solution by filtration to form a filter cake, which can thereafter be dried, calcined and loaded with the group VIII metal. The catalyst material is then formed into tablets, which tablets are crushed to form particles with a size of 250-500 µm, that can be used in a Fischer-Tropsch process. Additional post-treatments such as crushing, are required in order to obtain a catalyst powder for use in a slurry-phase process. However, the obtained average particle size, as indicated above, is still relatively large. Moreover, a lack of strength results in crushing to irregularly shaped particles and a broad particle size distribution. Catalysts with such large irregularly shaped particles and a broad particle size distribution tend to be less suitable for processes involving a bubble column, a slurry phase reactor or a loop reactor.

It has further been found that these conventional catalysts do not always satisfy the requirements with respect to mass transfer and/or heat transfer, when used in a catalytic process.

In addition, it has been found that—when used in a slurry phase process—separation properties, e.g. by filtration, are not particularly good, since a broad particle size distribution results in a very dense filtercake.

Further it has been found that the dispersion behaviour of these conventional catalysts—when used in a slurry phase process—is not particularly good, since the catalyst particles tend to agglomerate.

Other problems with commercially available zinc oxide supports suitable for loading with catalytic metal to form a catalyst, include inappropriate particle size distribution (in particular with supports obtained by precipitation), low surface area and pore volume, which typically makes them more difficult to impregnate, and several impregnation steps are required to deposit a reasonable amount of metal loading on the support. A low level of homogeneity of the metal distribution is obtained, once the metal has been applied. Further, the intrinsic strength of commercial zinc oxide particles is relatively low, making them strongly subject to attrition when used in a slurry-phase reactor.

In WO-A 03090925 a catalyst has been described comprising a cobalt and zinc coprecipitate having a specific particle size distribution. The catalyst of said invention has a very good mass and heat transfer in GTL processes.

It is an object of the present invention to provide a novel catalyst, suitable for use in Fischer-Tropsch synthesis, that may be used as an alternative to known catalysts, and which catalyst does not have at least some of the disadvantages of the various prior art catalyst, such as low strength and broad particle size distribution.

The invention is based on the surprising insight, that the use of a core-shell support based on an oxidic core and a zinc oxide shell, provides an excellent basis for preparing a zinc oxide based catalyst having a better attrition resistance than previously known catalysts.

Accordingly, the present invention relates to a catalyst, more in particular a Fischer-Tropsch catalyst, comprising a, preferably oxidic, core material, a shell of zinc oxide around said core material, and a catalytically active material in or on the shell, based on one or more of the metals cobalt, iron, ruthenium and/or nickel.

It has been found that a catalyst according to the present invention has very favourable properties for use in catalytic processes, more in particular gas to liquid FT-processes, wherein liquid hydrocarbons are prepared from synthesis gas. More in particular the catalyst of the invention has a superior strength, resulting in a very low abrasion of the material, thereby making it very suitable for those catalytic reactors that require strong catalyst particles.

Further, the catalyst according to the invention has been found to have particularly good mass and/or heat transfer properties, when used in a catalytic process.

A catalyst according to the invention has been found to be particularly favourable for use in a stirred slurry-phase reactor, bubble-column reactor, loop reactor or fluid-bed reactor.

A catalyst according to the invention shows very good flow properties in dry form and/or when used in a stirred slurry reactor, and good dispersibility properties with the reactants in the reaction mixture. The catalyst of the invention can be prepared in very appropriate particle size distribution, as indicated by the free-flowing properties of the dried catalyst, as can be observed, for example, when the catalyst is kept in a storage flask. This result is at least partly obtained by the fact that the oxidic core can be prepared separately before the application of the zinc oxide shell.

A catalyst according to the invention shows very favourable separation properties and can for example very suitably be separated from the reaction mixture by filtration.

A catalyst according to the invention has an extremely good balance between activity and separation properties.

Preferably the catalyst of the present invention has mainly (i.e. at least 75 vol. %) pores having a diameter in the range of 1-15 nm. Much preferred is a catalyst having essentially no pores with a diameter of less than 5 nm (in particular less than 5% of the pore volume formed by pores with a diameter of less than 5 nm). It has been found that such a catalyst has particularly good diffusion properties for reactant and product. Such a catalyst has also been found to be highly selective towards the Fischer-Tropsch reaction.

Very good results have been achieved with a catalyst having a pore volume of less than 0.5 ml/g. The pore volume is preferably at least 0.05 ml/g. Particularly suitable is a catalyst with an pore volume of less than 0.45 ml/g.

The pore volume of the catalyst is determined by nitrogen adsorption ($N_2$-BET), measured on an Ankersmit Quantachrome Autosorb-6 apparatus, after degassing the sample at 180° C. to a pressure of 3.3 Pa (25 mTorr).

Such a catalyst has been found to have particularly good physical strength properties, which is advantageous in applications in various types of reactors, including slurry-phase reactors, loop-reactors, bubble-column reactors and fluid-bed reactors.

Also the surface area—as determined by nitrogen adsorption ($N_2$-BET) by an Ankersmit Quantachrome Autosorb-6 apparatus, after degassing at 180° C. down to a pressure of 3.3 Pa (25 mTorr), can be chosen within the wide range, depending upon the intended purpose. For a Fischer-Tropsch process, this parameter may for example be chosen in the range of 1-500 $m^2/g$. Preferably a catalyst has a surface area in the range of 5-160 $m^2/g$. Very good results have been achieved with a catalyst having a surface area in the range of 5-150 $m^2/g$.

A preferred catalyst according to the invention is a particulate material wherein the particles have a more or less spherical geometry. Such a catalyst has been found to have very good strength and separation properties, and a relatively high attrition resistance during use.

The composition of the catalyst can be varied widely, which composition the skilled professional will know to determine, depending upon the intended purpose.

The catalyst may essentially consist of cobalt, iron, ruthenium and/or nickel as the metallic component. It is however also possible that the catalyst contains one or more other components, such as components that are commonly employed as promoters in Fischer-Tropsch catalysts. The catalyst may also contain one or more promoters, for example hafnium, platinum, zirconium, palladium, rhenium, cerium, lanthanum or a combination thereof. When present, such promoters are typically used in an atomic ratio of metallic component to promoter of up to 10:1.

The catalyst according to the invention contains a core that preferably comprises oxidic materials, for example oxides based on silicon (Si), aluminium (Al), gallium (Ga), zirconium (Zr) and titanium (Ti), or combinations thereof. In the preferred embodiment, aluminium is particularly preferred. It is to be noted that the material of the core does not contain zinc oxide. More in particular, the process of producing the core-shell support is such, that substantially no zinc oxide will be present inside the core material.

In another embodiment, the internal core comprises other materials, for example carbides (e.g. silicon carbide) or clay-based structures (e.g. kaolins and montmorillonites).

In general the catalyst may be prepared by a method wherein a zinc oxide layer is applied on the surface of the core material, optionally after applying an intermediate layer of another oxide, such as silica, tungsten oxide, or alumina. Between the application of the various layers, it is possible to wash and/or dry and/or calcine the material, however, this is not necessary.

After the core-shell support has been produced, the catalytically active material is applied thereon by suitable applications means, such as impregnation, deposition precipitation, or by use of the so-called layer-by-layer method. In general, a salt of the cobalt, iron, ruthenium and/or nickel metal to be applied as catalytic material is brought onto the zinc oxide surface by suitable means, followed by calcination and hydrogenation to produce the metal based catalyst.

Various methods, such as spray drying, are suitable for the application of the zinc oxide shell on the core. It is preferred to use a method based on the so-called Layer-By-Layer (LBL) method.

The present invention further relates to a method for preparing a catalyst as discussed above, by depositing a zinc oxide layer as a shell onto the core material particles, thereby applying electrostatic deposition of at least one material onto another by utilizing charge reversal, including the use of ionic charge reversing agents to produce a suitable catalyst support precursor by the use of the Layer-By-Layer (LBL) method.

Examples of this prior art LBL technique are described in Valtchev et al, Microporous and Mesoporous Materials, 43 (2001) 41-49; Wang et al., Chemical Communications, 2161 (2000) and Millward et al., Chemical Communications, 1994 (2001). Also in Hoogeveen et al, Polyelectrolyte adsorption on Oxides I and II, J of Colloid and interface Science 182, 133-145 (1996), and 182, 145-157 (1996) the adsorption of charged polyelectrolytes on oxide surfaces has been discussed.

U.S. Pat. No. 5,208,111 describes multi-layered layer elements applied to supports using materials of opposite charge in consecutive layers. In U.S. Pat. No. 6,022,590 to Ferguson, the stepwise formation of multilayered structures is described, involving the alternate adsorption of a cationic polyelectrolyte and anionic sheets of a silicate clay onto a substrate.

In general, the use of the LBL method implies the alternate adsorption of oppositely charged ionic species onto the surface of a substrate (the core material), thereby reversing the charge thereof, as discussed hereafter.

Advantages of the LBL method in preparing the catalyst of the present invention include excellent control over layer thickness, the ability to incorporate layers of varying chemical composition, as well as the fact that the method is experimentally straightforward and can be performed at room temperature in an aqueous medium. The deposition reactions are fast even at room temperature.

After loading the core material with at least one charged ionic species, the coated core material is optionally provided with an oxide layer, by applying a precursor for the oxide (such as silica, tungsten oxide, or alumina), prior to applying the zinc oxide, preferably as a colloidal solution to the core material.

Materials for applying the intermediate oxide layer are suitably the general oxide precursors, such as colloidal oxide solutions, polyoxometalcations or polyoxometallates.

Loading of charged ionic species and ZnO (with or without an oxide) is typically performed in a series of consecutive steps, followed by calcination, as desired. In a subsequent step, the so-obtained support material is loaded with the catalyst precursor metal selected from cobalt, iron, ruthenium and nickel, by incipient wetness impregnation, using an aqueous solution of a salt of the metallic component. In this stage also the promoter may be applied.

This invention specifically refers to a preferred method of preparing the catalyst by loading the core material with at least one charge reversing ionic species, dispersing the coated core material in a molecular or colloidal oxide precursor solution, such as of silica, treating the material again with at least one charge reversing ionic species and dispersing the said treated core material into a colloidal ZnO solution.

This method has been found to be particularly suitable for preparing a catalyst as described above.

In a more specific embodiment, the invention concerns the preparation of a robust support, namely alumina, with zinc oxide using layer-by-layer controlled surface coating. It additionally discloses the deposition of a second inorganic oxide between the alumina and zinc oxide layers as an intermediate between the zinc oxide layer and the substrate particle. These depositions rely on charge reversal, and the charge on the substrate particle can be altered as desired by using charged ionic materials such as poly diallyldimethylammonium chloride (denoted PDADMAC) or poly sodium styrene sulfonate (PSS) in aqueous solutions.

The charged ionic species, or charge reversing agents, that may be used in the present invention include monomeric species, oligomeric materials and low, medium, and high molecular weight polymers, for example in the range of up to about 1,000,000, more in particular of about 200 to about 1,000,000. Monomeric species may be selected from various suitable ionic species, such as diallyldimethylammonium chloride or styrene sulfonic acid salt and the like. An example of a cationic inorganic oxide precursor would be aluminum chlorohydrol (also known as the Keggin ion); an example of an anionic polyoxometallate is ammonium metatungstate.

Examples of polymeric species capable of forming large polyanions, when ionized, are well known. A preferred polymeric species is a water-soluble vinyl polymer, or an alkali metal or ammonium salt thereof, or an alkali metal or ammonium salt of polysilicic acid. Specific examples include poly (acrylic) acids, poly (methacrylic) acids, substituted poly (acrylic acid), substituted poly (methacrylic acid), or an alkali metal or an ammonium salt of any of these acids. One commercially available anionic species is sodium polyacrylate.

Further examples of suitable polymeric species useful in the present invention are disclosed in U.S. Pat. No. 5,006,574. One useful water-soluble cationic polymeric material is a diallyl quaternary ammonium polymer salt. This cationic polymer is characterized by a high density of positive charge. Preferably, the polymer does not have negative groups such as carboxyl or carbonyl groups.

U.S. Pat. No. 5,006,574 also discloses other quaternary ammonium cationic polymers obtained by copolymerizing an aliphatic secondary amine with epichlorohydrin. Still other water-soluble cationic polyelectrolytes are poly (quaternary ammonium) polyester salts that contain quaternary nitrogen in a polymeric backbone and are chain extended by the groups. They are prepared from water-soluble poly (quaternary ammonium salts) containing pendant hydroxyl groups and bi-functionally reactive chain extending agents. Such polyelectrolytes are prepared by treating N,N,N',N'-tetraalkylhydroxyalkylene diamine and an organic dihalide such as dihaloalkane or dihaloether with an epoxy haloalkane. Other water-soluble cationic polyelectrolytes are polyamines, such as for instance polyallylamine hydrochloride, and alkylphosphonium salts.

Cationic polymeric species are also commercially available. For instance a cationic oligomer is marketed by Calgon Corp. under the trademark "CALGON 261" and another marketed by Nalco Chemical Co. under the trademark "NALCO 7607", and poly(sodium 4-styrene sulfonate) is available from National Starch and Chemical under the trademark "Flexan 130".

In the deposition phase, a solution of the ionic charge reversing species to be deposited is first prepared. The pH of this solution can be adjusted as desired to control surface charge characteristics. In addition, an inorganic salt such as sodium chloride can be dissolved in the said solution to control the ionic strength of the solution. A measured amount of substrate (core material) is added to the said solution, and the mixture stirred at room temperature for the desired deposition time (typically 1-30 minutes). Following deposition, the substrate is collected from solution by filtration, and washed with an excess of deionized water to remove excess, unattached charged ionic species.

The substrate is then re-slurried in a solution of the second coating layer that possesses a charge opposite to that of the first charged species. The deposition process is repeated, and the substrate collected in the same way. This series of deposition steps can be repeated as many times as desired by alternately subjecting the substrate to positively and negatively charged ionic species.

The preferred material used to produce a positive surface charge on the substrate is poly-(diallyldimethylammonium chloride), denoted PDADMAC. In this material, the diallyldimethylammonium fragment confers the positive charge on the substrate surface, and the negative counter ion is the chloride anion. PDADMAC is hence considered to be the "positive polymer". This material is available commercially with a variety of molecular weights, and may be used here with a molecular weight of approximately 200 to 1,000,000.

The preferred polymer used to provide a negative surface charge is poly (sodium 4-styrene sulfonate), denoted PSS. In this case the positive counter ion is sodium, and the styrene sulfonate confers a negative surface charge to the substrate. PSS may be used with a molecular weight of up to approximately 1,000,000, and can be used in the form of a solid or aqueous solution.

The inorganic materials used for this work are preferably colloidal zinc oxide and colloidal silica, with a preferred particle size of <150 nm. Other inorganic oxides may be used with equal success.

The polymeric materials are used to manipulate the charge on the substrate particles to promote the deposition of the inorganic oxides. In order to make the oxide deposition more effective, the substrate is preferably treated with PDADMAC.

It is to be noted, that it is possible to repeat the application of the various layers one or more times, with or without intermediate filtration by sequential addition of controlled amounts of charge reversing agents. This gives the possibility to regulate the thickness of the various layers, the diameter of the particles and the attrition behavior.

When the deposition process has been completed, the sample is calcined in air to remove the charged layers, leaving a material composed primarily of inorganic oxides. Following calcination, the materials may be recovered and examined by elemental analysis. Certain property measurements may also be undertaken, such as the measurement of particle size distribution after an attrition test. In addition, impregnation of the support with a suitable metal precursor, such as cobalt, iron, ruthenium and/or nickel, may be performed via standard techniques prior to performance evaluation in a selected catalytic reaction. The amount of catalytically active material is between 5 and 50 wt. % of the total weight of the catalyst.

A typical experimental procedure is detailed below as Example 1 for depositing a combination of silica and zinc oxide on alumina. The isoelectric point of oxides and hydroxides of aluminum can vary considerably depending on composition, form and experimental conditions, mostly in the pH range 5 to 10 (Parks, Chemical Reviews (1965), pages 177-198).

The present invention further relates to the use of a catalyst according to the invention in a slurry reactor, a loop reactor, a bubble-column reactor or a fluid-bed reactor. The present invention further relates to the use of a catalyst according to the invention in a Fischer-Tropsch process or a functional group hydrogenation process, such as nitrile hydrogenation to amines.

The invention is further illustrated by the following examples.

EXAMPLE 1

Catalyst Preparation

A solution was prepared consisting of 1.5 g PSS (sodium polystyrene sulfonate, MW 70,000) in 114 g of 0.1 M aqueous NaCl, and the pH adjusted to ~5 using 0.1 M aqueous hydrochloric acid. To this solution was added 30 g of Condea SB Alumina, and the mixture stirred for 15 minutes at room temperature. After 15 minutes, the substrate was recovered by filtration and washed with an excess of deionized water.

The substrate was then treated with a solution comprising 3 g PDADMAC (poly diallyldimethylammonium chloride, MW 100,000 to 200,000) in 114 g of 0.1 M aqueous NaCl, adjusted to approximately pH 9 using 0.1 M ammonia solution. After stirring for 15 minutes at room temperature, the substrate was recovered by filtration and washed with an excess of deionized water.

The substrate was then slurried in 1% colloidal $SiO_2$ (Nalco 2327, 20 nm particle size) in 0.1 M aqueous NaCl. The pH was not adjusted (pH ~9). After stirring for 15 minutes, the solid was recovered by filtration and washed with an excess of deionized water.

The substrate was then treated with a solution comprising 3 g PDADMAC (poly diallyldimethylammonium chloride) in 114 g of 0.1 M aqueous NaCl, adjusted to approximately pH 9 using 0.1 M ammonia solution. After stirring for 15 minutes at room temperature, the substrate was recovered by filtration and washed with an excess of deionized water.

The substrate was then slurried in 1% colloidal ZnO (Nyacol DP5370, 50 nm particle size) in 0.1 M aqueous NaCl. The pH was not adjusted. After stirring for 15 minutes, the solid was recovered by filtration and washed with an excess of deionized water.

The substrate was then treated with 2 further treatments of (PDADMAC+ZnO) applied in an alternating manner as described above. The catalyst support was then dried at 90° C. in air. At this point, the composition of the material could be described as follows:

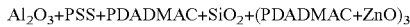

$Al_2O_3$+PSS+PDADMAC+$SiO_2$+(PDADMAC+ZnO)$_3$

Following calcination in flowing air at 600° C., the catalyst was characterized for its chemical composition and physical properties. The silicon content was determined to be 1.5% w/w Si on a VF basis, corresponding to 3.2% w/w $SiO_2$. The zinc content was determined to be 12.4% w/w Zn on a VF basis, corresponding to 15.4% w/w ZnO.

The so-obtained coated support was subsequently loaded with 20% cobalt, by porevolume impregnation, thereby dissolving cobaltnitrate in the required volume of demiwater and impregnating this to the support material. After drying at 110° C., the material was calcined at 500° C. for 5 hours. The analytical data of this catalyst are presented in table 1.

EXAMPLE 2

Catalyst Preparation

A zinc oxide-coated alumina material was prepared in an analogous manner to Example 1, except that no silica was used. After calcination in air, the final zinc content was determined to be 2.0% w/w Zn, corresponding to 2.5% w/w ZnO.

Other chemical and physical properties of the ultimate catalyst are presented in table 1.

EXAMPLE 3

Catalyst Preparation

A 1% w/w solution of PSS was prepared in 0.1 M aqueous NaCl, and the pH adjusted to ~5 using 0.1 M aqueous hydrochloric acid. To 200 ml of this solution, 30 g of Condea SB Alumina was added, and the mixture stirred for 15 minutes at room temperature. After 15 minutes, the substrate was recovered by filtration and washed with an excess of deionized water.

The substrate was then slurried in 200 ml of a 1% w/w solution of PDADMAC in 0.1 M aqueous NaCl, adjusted to pH 9.5 using 0.1 M ammonia solution. Contact time was 15 minutes at room temperature under continuous agitation. Following this treatment, the substrate was collected by filtration and washed with deionized water to remove excess, unattached polymer.

The substrate was then slurried in 1% colloidal ZnO (Nyacol DP5370, 50 nm particle size) in 0.1 M aqueous NaCl. The pH was not adjusted. After stirring for 15 minutes, the solid was recovered by filtration and washed with an excess of deionized water.

The substrate was then treated with 2 further treatments of (PDADMAC+ZnO) applied in an alternating manner as described above. The catalyst support was then dried at 90° C. in air. At this point, the alumina composition can be described as $Al_2O_3$+PSS+(PDADMAC+ZnO)$_3$. Following calcination in flowing air at 550° C., the catalyst was characterized for its chemical composition. Elemental analysis showed 13.0% w/w Zn on a volatile free basis, corresponding to 16.2% w/w ZnO.

EXAMPLE 4

Catalyst Preparation—Comparative Experiment

A metal solution (1000 ml) containing 21.0 g/l cobalt and 64.2 g/l zinc was prepared by dissolving 292.4 g of $Zn(NO_3)_2.9H_2O$ and 103.8 g of $Co(NO_3)_2.6H_2O$ in 1000 ml of demineralised water. The base solution was prepared by dissolving 142 g of $(NH_4)_2CO_3$ in 1000 ml of demineralised water. The metal and base solution were injected simultaneously at equal flow rates (1000 ml/hr) into a well stirred, baffled precipitation vessel containing 1750 ml of demineralised water. The temperature during precipitation was maintained at 75° C.

The pH was kept constant at pH 6.2 by providing acid solution and alkaline solution at equal addition rates.

The resulting precipitate was washed with demineralised water and dried overnight at 110° C. The dried catalyst was heated from room temperature with 150° C./hr to 500° C. and calcined for 5 hours at 500° C.

The chemical and physical properties of this catalyst are presented in table 1.

TABLE 1

Physical and chemical properties of the catalysts.

|  |  | Catalyst Example 1 | Catalyst Example 2 | Comparative catalyst (Example 4) |
|---|---|---|---|---|
| Cobalt content | wt % | 19.3 | 20.0 | 20 |
| Zn content | wt % | 12.4 | 2.0 | 80 |
| Si content | wt % | 1.5 | — | — |
| BET-surface area | m$^2$/g | 106 | 133 | 28 |
| N$_2$ pore volume | ml/g | 0.29 | 0.34 | 0.19 |
| Particle size distribution |  |  |  |  |
| D(v. 0.9)[1] | μm | 92 | 92 | 30.3 |
| D(v. 0.5)[1] | μm | 38 | 38 | 23.1 |
| D(v. 0.1)[1] | μm | 8 | 8 | 17.9 |
| Span[1] |  | 2.3 | 2.3 | 0.5 |
| Crystallite size[2] | Å | 140 | 137 | 150 |
| Fines upon attrition[3] | % | 2 | n.d. | 4 |

Ad 1: The span is calculated from the measured Malvern particle size distribution and gives an indication for the broadness of the particle size distribution, as is defined as follows:

$$\text{Span} = \frac{D[v, 0.9] - D[v, 0.1]}{D[v, 0.5]}$$

wherein:

D[v,0.9]=particle size (μm) below which 90% of particles exists (in Malvern volume particle size distribution).

D[v,0.5]=particle size (μm) below which 50% of particles exists (in Malvern volume particle size distribution).

D[v,0.1]=particle size (μm) below which 10% of particles exists (in Malvern volume particle size distribution).

Ad 2: The Co$_3$O$_4$ crystallite size, as reported in table 1, is calculated from the XRD spectrum, particularly from the d=2.03 line in the XRD pattern (CuKα-radiation).

Ad 3: The physical strength of the powder particles was determined in a liquid-phase attrition test, by slurrying 5.0 grams of catalyst powder in 200 mls of demiwater, and treating the slurry in a blender (Waring, type 33BL79), operating at 15,000 RPM for 6 minutes. Fines were defined as the particles below 5 μm.

The cobalt content herein was measured by X-ray fluorescence.

EXAMPLE 5

Measurement of the Particle Size Distribution

The particle size distribution of a catalyst according to the invention was measured on a Malvern Mastersizer MS 20.

The sample vessel of the apparatus was filled with demineralized water, and diffraction of measuring-cell filled with water was determined (for background correction). An appropriate amount of catalyst powder was then added to the sample vessel, which was treated in ultrasonic bath for 3 minutes (25% of max. output u.s. power) and stirring (50% of max. stirring speed), prior to the measurement. After this treatment, the sample was measured and the measured diffraction signal was corrected for the 'background' measurement.

Calculation of particle size distribution was done using the following parameters: Model: Model Independent; Presentation: 1907; Particle size distribution: Volume distribution.

EXAMPLE 6

Activity Test

A sample (2 ml) of the catalyst of Example 1 was diluted with 8 ml inert alumina and loaded into a fixed-bed reactor (9 mm diameter). The catalyst was first heated at 250° C. (60° C./h) under air. After a dwell for 2 hours at 250° C., the air was replaced by nitrogen, applying this condition for 0.2 hours. The reduction was started by introducing carbon monoxide (at 250° C.) for 3.5 hours. The carbon monoxide was then replaced by nitrogen, dwell for 0.2 hours. In a subsequent step, the reduction was completed under hydrogen for 1.5 hour, still at 250° C. The reactor was then cooled down to a temperature below 90° C. The Fischer-Tropsch test was started up by feeding syngas (hydrogen/carbonmoxide ratio 2:1) to the reactor at GHSV 8000 h$^{-1}$. The reactor was then slowly heated up until the required CO conversion was obtained.

After 40 hours on stream a C5+ productivity of 493 g/litre of catalyst/hr was obtained at a temperature of 238° C.

EXAMPLE 7

Activity Test—Comparative Test

A sample of catalyst (2 ml) made according to Example 4 (comparative preparation) was reduced and activated according to the same method as described in Example 6.

After such activation, this catalyst showed a C5+ productivity of 558 g/litre of catalyst/hr, obtained at a temperature of 225° C.

What is claimed is:

1. A process for producing liquid hydrocarbons by a Fischer-Tropsch process in the presence of a Fischer-Tropsch catalyst comprising an active catalytic material of one or more metals selected from the group consisting of cobalt, iron, ruthenium, and nickel, the improvement comprising the catalyst comprising a core material, a shell of zinc oxide around said core material, and a catalytically active material in or on the shell, said catalytically active material comprising one or more metals selected from the group consisting of cobalt, iron, ruthenium and nickel, wherein the catalyst has a surface area in the range of 5-160 m$^2$/g, and the amount of catalytically active material is between 5 and 50 wt. % of the total weight of the catalyst.

2. The process according to claim 1, wherein the process is carried out in a slurry reactor, a loop reactor, a bubble column, or a fluid bed reactor.

3. The process according to claim 1, wherein the core material comprises at least one material selected from group consisting of silica, alumina, silica-alumina, titania, zirconia, Si-carbides, synthetic clay materials, and natural clay materials.

4. The process according to claim 1, wherein the catalyst has pores, at least 75 vol. % of the pores have diameter in the range of 1-15 nm, and less than 5 vol. % of said pores have a diameter of less than 5 nm.

5. The process according to claim 1, wherein the shell of zinc oxide is between 1 and 30 wt. % of the combined weight of the core and the shell.

6. The process according to claim 1, wherein the catalyst has a surface area in the range of 5-150 m²/g.

7. The process according to claim 1, wherein the catalytically active material is cobalt.

8. A process for producing liquid hydrocarbons by a Fischer-Tropsch process in the presence of a Fischer-Tropsch catalyst comprising an active catalytic material of one or more metals selected from the group consisting of cobalt, iron, ruthenium, and nickel, the improvement comprising the catalyst comprising a core material, a shell of zinc oxide around said core material, and a catalytically active material in or on the shell, said catalytically active material comprising one or more metals selected from the group consisting of cobalt, iron, ruthenium and nickel, wherein the catalyst has pores and at least 75 vol. % of the pores have diameter in the range of 1-15 nm, and wherein the amount of catalytically active material is between 5 and 50 wt. % of the total weight of the catalyst.

9. The process according to claim 8, wherein the process is carried out in a slurry reactor, a loop reactor, a bubble column, or a fluid bed reactor.

10. The process according to claim 8, wherein less than 5 vol. % of the pores have a diameter of less than 5 nm.

11. The process according to claim 8, wherein said core material comprises at least one material selected from group consisting of silica, alumina, silica-alumina, titania, zirconia, Si-carbides, synthetic clay materials, and natural clay materials.

12. The process according to claim 8, wherein less than 5 vol. % of the pores have a diameter of less than 5 nm.

13. The process according to claim 8, wherein the shell of zinc oxide is between 1 and 30 wt. % of the combined weight of the core and the shell.

14. The process according to claim 8, wherein the catalyst has a surface area in the range of 5-150 m²/g.

15. A process for producing amines by a functional group hydrogenation process in the presence of a catalyst comprising an active catalytic material of one or more metals selected from the group consisting of cobalt, iron, ruthenium, and nickel, the improvement comprising the catalyst comprising a core material, a shell of zinc oxide around said core material, and a catalytically active material in or on the shell, said catalytically active material comprising one or more metals selected from the group consisting of cobalt, iron, ruthenium and nickel, wherein the catalyst has a surface area in the range of 5-160 m²/g, and the amount of catalytically active material is between 5 and 50 wt. % of the total weight of the catalyst.

16. The process according to claim 15, wherein the process is carried out in a slurry reactor, a loop reactor, a bubble column, or a fluid bed reactor.

17. The process according to claim 15, wherein the core material comprises at least one material selected from group consisting of silica, alumina, silica-alumina, titania, zirconia, Si-carbides, synthetic clay materials, and natural clay materials.

18. The process according to claim 15, wherein the catalyst has pores, at least 75 vol. % of the pores have diameter in the range of 1-15 nm, and less than 5 vol. % of said pores have a diameter of less than 5 nm.

19. The process according to claim 15, wherein the shell of zinc oxide is between 1 and 30 wt. % of the combined weight of the core and the shell.

20. The process according to claim 15, wherein the catalyst has a surface area in the range of 5-150 m²/g.

* * * * *